(12) United States Patent
Weng (10) Patent No.: US 11,624,742 B2
(45) Date of Patent: Apr. 11, 2023

(54) PHOTONIC CRYSTAL GAS SENSOR

(71) Applicant: The Board of Regents of the University of Oklahoma, Norman, OK (US)

(72) Inventor: Binbin Weng, Norman, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 241 days.

(21) Appl. No.: 17/074,448

(22) Filed: Oct. 19, 2020

(65) Prior Publication Data

US 2021/0116433 A1 Apr. 22, 2021

Related U.S. Application Data

(60) Provisional application No. 62/916,907, filed on Oct. 18, 2019.

(51) Int. Cl.
| | | |
|---|---|---|
| *G01N 33/00* | (2006.01) | |
| *G01N 21/3504* | (2014.01) | |
| *G01N 21/25* | (2006.01) | |
| *G01N 21/61* | (2006.01) | |
| *G01N 21/63* | (2006.01) | |

(52) U.S. Cl.
CPC ......... *G01N 33/0044* (2013.01); *G01N 21/25* (2013.01); *G01N 21/3504* (2013.01); *G01N 33/0042* (2013.01); *G01N 21/61* (2013.01); *G01N 2021/633* (2013.01)

(58) Field of Classification Search
CPC ........... G01N 33/0044; G01N 21/3504; G01N 21/61; G01N 21/62; G01N 21/63; G01N 2021/633; G01N 21/636; G01N 2021/1725; G01N 2021/3125
See application file for complete search history.

(56) References Cited

U.S. PATENT DOCUMENTS

| | | | |
|---|---|---|---|
| 7,267,948 | B2 | 9/2007 | Vo-Dinh |
| 7,483,130 | B2 | 1/2009 | Baumberg et al. |
| 3,003,408 | A1 | 8/2011 | Zhang et al. |
| 8,687,187 | B2 | 4/2014 | Cunningham |
| 8,830,450 | B2 | 9/2014 | Bond et al. |

(Continued)

FOREIGN PATENT DOCUMENTS

WO 2018132564 A1 7/2018

OTHER PUBLICATIONS

Hemati, Tahere, et al.; "A Direct Oriented-Attachment Growth of Lead-Chalcogenide Mid-Infrared Nanocrystals Film an Amorphous Substrates"; Journal of Materials Chemistry C; Issue 38; 2020; 7 pages.

(Continued)

*Primary Examiner* — Benjamin R Schmitt
(74) *Attorney, Agent, or Firm* — Conley Rose, P.C.; Grant Rodolph; Jonathan K. Polk (57) ABSTRACT

A gas sensor comprising: a substrate; a grating array disposed on top of the substrate and comprising grates; and voids defined by the grates and configured to confine gas molecules for absorption of light and analysis. A method of gas sensing comprising: generating first light; converting the first light into second light using grates of a grating array; resonating the second light within the grating array; confining gas molecules in voids defined by the grates; and causing the gas molecules to absorb the second light within the voids.

19 Claims, 7 Drawing Sheets

(56) References Cited

U.S. PATENT DOCUMENTS

| | | | |
|---|---|---|---|
| 9,213,000 | B2 | 12/2015 | Ozin et al. |
| 9,272,126 | B2 | 3/2016 | Cunningham et al. |
| 9,632,032 | B2 | 4/2017 | Landis et al. |
| 9,733,125 | B2 | 8/2017 | Liu et al. |
| 10,466,167 | B2 | 11/2019 | Nayak et al. |
| 2005/0176029 | A1 | 8/2005 | Heller et al. |
| 2005/0186565 | A1 | 8/2005 | Malak |
| 2006/0055920 | A1 | 3/2006 | Wang et al. |
| 2006/0055921 | A1 | 3/2006 | Wang et al. |
| 2006/0056463 | A1 | 3/2006 | Wang et al. |
| 2006/0147148 | A1 | 7/2006 | Wang et al. |
| 2010/0085566 | A1 | 4/2010 | Cunningham |
| 2011/0128537 | A1 | 6/2011 | Bond et al. |
| 2011/0176130 | A1 | 7/2011 | Gu et al. |
| 2012/0078523 | A1 | 3/2012 | Letant et al. |
| 2012/0276549 | A1 | 11/2012 | Cunningham et al. |
| 2012/0281209 | A1 | 11/2012 | Bai |
| 2013/0169960 | A1 | 7/2013 | Cunningham |
| 2013/0171667 | A1 | 7/2013 | Unnimadhava Kurup Soudamini Amma et al. |
| 2014/0193839 | A1 | 7/2014 | Cunningham |
| 2014/0322729 | A1 | 10/2014 | Fan et al. |
| 2015/0322286 | A1 | 11/2015 | Cabrini et al. |
| 2017/0356850 | A1 | 12/2017 | Gu et al. |
| 2018/0003706 | A1 | 1/2018 | Trenholm et al. |
| 2019/0033218 | A1 | 1/2019 | Gong et al. |
| 2020/0205667 | A1 | 7/2020 | Unnimadhava Kurup Soudamini Amma et al. |

OTHER PUBLICATIONS

Hemati, Tahere, et al.; "Theoretical Study of Leaky-Mode Resonant Gratings for Improving the Absorption Efficiency of the Uncooled Mid-Infrared Photodetectors"; J. Appl. Phys. vol. 124; Aug. 6, 2018; 7 pages.

Rahomaki, Jussi, et al.; "Horizontal Slot Waveguide Channel for Enhanced Raman Scattering"; Optics Express; vol. 21, Issue 7; 2013; 9 pages.

Weng, Binbin, et al. "Continuous-Wave Mid-Infrared Photonic Crystal Light Emitters at Room Temperature"; Appl. Phys. B.; vol. 123; Dec. 26, 2016; 5 pages.

Weng, Binbin, et al.; "Responsivity Enhancement of Mid-Infrared PbSe Detectors Using CaF2 Nano-Structured Antireflective Coatings"; Appl. Phys. Lett.; vol. 104; Jan. 14, 2014; 5 pages.

PCT International Search Report; Application No. PCT/US2020/020454; dated May 20, 2020; 3 pages.

PCT Written Opinion of the International Searching Authority; Application No. PCT/US2020/020454; dated May 20, 2020; 12 pages.

PHOTONIC CRYSTAL GAS SENSOR

CROSS-REFERENCE TO RELATED APPLICATIONS

This claims priority to U.S. Prov. Patent App. No. 62/916,907 filed on Oct. 18, 2019 by The Board of Regents of the University of Oklahoma and titled "Gas Sensor Based on Active Photonic Crystal in Mid-Infrared Spectrum," which is incorporated by reference.

BACKGROUND

Sour gas refers to natural gas containing significant amounts of acidic gases such as $H_2S$ and $CO_2$. About 50% of the world's natural gas is sour gas. The United States, which is the largest gas producer in the world, has a high concentration of sour gas. As demand for and production of gas increase, it will become more important to effectively produce and transport sour gas.

Sour gas can damage drilling equipment during production and can corrode piping during production and transportation, thus requiring the use of corrosion-resistant nickel-alloy or stainless-steel materials, which are more expensive. In addition, treating sour gases with sweeteners and recovery units is expensive. Furthermore, some sour gases such as $H_2S$ are highly toxic and flammable. For instance, an $H_2S$ concentration over 600 ppm can be instantly lethal, and an $H_2S$ concentration over 43,000 ppm can cause explosions. There is therefore a desire to reduce or eliminate acidic gases from natural gas.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

A number of sensors have been developed to measure acidic gas concentration. Those sensors include gold film analyzers, lead-acetate cassette-tape detectors, electrochemical detectors, and colorimetric detection tubes. However, those sensors suffer from a lack of portability, chemical interference, long response times, a need for frequent calibration and maintenance, sensitivity to environmental factors such as temperature and humidity, false alarms and missed alarms, and other shortcomings. There is therefore a desire for an acidic gas sensor that overcomes those shortcomings.

Disclosed herein are embodiments for a photonic crystal gas sensor. The photonic crystal gas sensor, or simply gas sensor, may be part of a larger gas sensor system. The gas sensor comprises a grating array with grates made of solid-state materials that increase light wavelength for absorption by, and thus sensing of, specific gases. The sensing is in-situ, real-time sensing. The gases are acidic gases, for instance $H_2S$, so that the gas sensor is an acidic gas sensor. By sensing acidic gases, the gas sensor protects people, protects infrastructure, and assesses costs of remediation of acidic gases. The gas sensor has applications in the oil and gas industry, specifically upstream oil and gas, as well as the health and environmental industries. The gas sensor has a long lifespan of over 10 years due to its use of solid-state materials, has a small size, has a low cost due to use of a low-wavelength optical source, has high performance, and needs little or no recalibration. In addition, the gas sensor is sealed off from outside elements both through its solid-state structure and a protective coating on the grates, thus further extending the life of the gas sensor.

Before describing various embodiments of the present disclosure in more detail by way of exemplary description, examples, and results, it is to be understood as noted above that the present disclosure is not limited in application to the details of methods and apparatus as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and apparatus of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges (e.g., in units of length such as micrometers or millimeters) include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. For example, a reference to a range of 3 mm and 20 mm in diameter, or a range of 50 µm to 300 µm in thickness, is intended to explicitly include all units of measurement in the range.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error. Further, in this detailed description, each numerical value (e.g., temperature or time) should be read once as modified by the term "about" (unless already expressly so modified), and then read again as not so modified unless otherwise indicated in context. As noted above, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. Unless otherwise stated, the terms "about" or "approximately", where used herein when referring to a measurable value such as an amount, length, thickness, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The following abbreviations apply:
ASIC: application-specific integrated circuit
$BaF_2$: barium fluoride
C: carbon
$CaF_2$: calcium fluoride
CBD: chemical bath deposition
$CO_2$: carbon dioxide
CPU: central processing unit
$C_1$: methane
$C_2$: ethane
$C_3$: propane
$C_4$: butane
DSP: digital signal processor
e-beam: electron-beam
EO: electrical-to-optical
FPGA: field-programmable gate array Ge: germanium
H$_2$S: hydrogen sulfide
IR: infrared
IUPAC: International Union of Pure and Applied Chemistry
mm: millimeter(s)
mV: millivolt(s)
nm: nanometer(s)
OE: optical-to-electrical
Pb: lead
PeSe: lead selenide
ppm: part(s) per million
PVD: physical vapor deposition
RAM: random-access memory
RF: radio frequency
ROM: read-only memory
RX: receiver unit
S: sulfur
Se: selenium
Si: silicon
SiO$_2$: silicon dioxide
Sn: tin
SRAM: static RAM
TCAM: ternary content-addressable memory
Te: tellurium
TX: transmitter unit
ZnSe: zinc selenide
μm: micrometer(s)
2D: two-dimensional.

Figure 1A:
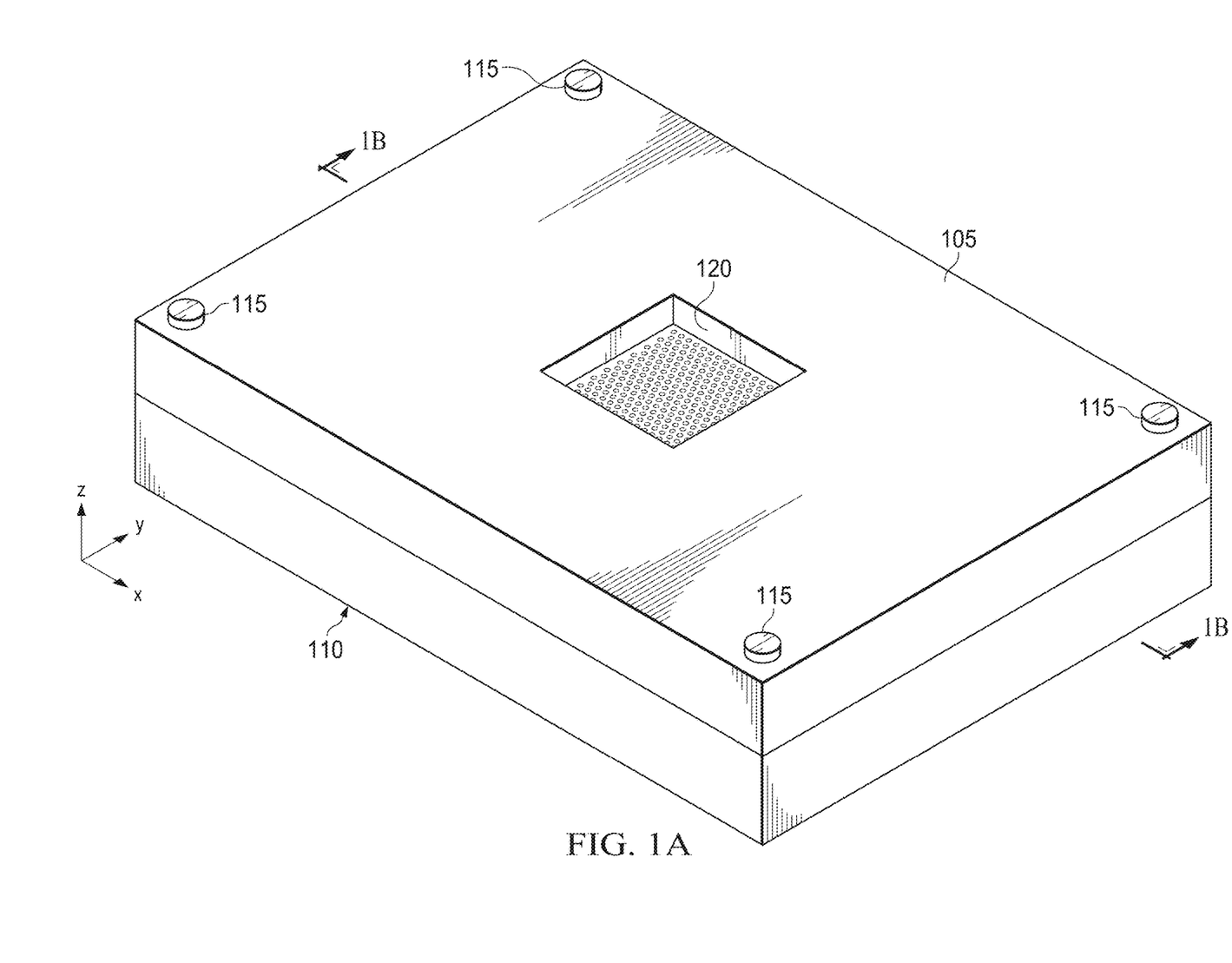
FIG. 1A is a schematic diagram of a gas sensor.

FIG. 1A is a schematic diagram of a gas sensor 100. The gas sensor 100 may also be referred to as a gas detector. In an example, the gas sensor 100 is less than 2" in length in the x direction, 1" in width in the y direction, and 0.5" in height in the z direction. The gas sensor 100 comprises a top 105, a bottom 110, four screws 115, and a gas entryway 120. The top 105, the bottom 110, and the screws 115 comprise plastic, metal, or another suitable material. The top 105 and the bottom 110 are bonded to each other during manufacturing by, for instance, using an adhesive. In addition, the top 105 and the bottom 110 are fastened to each other during manufacturing using the screws 115. The gas entryway 120 is a hole or other structure that allows gas to enter the gas sensor 100.

Figure 1B:
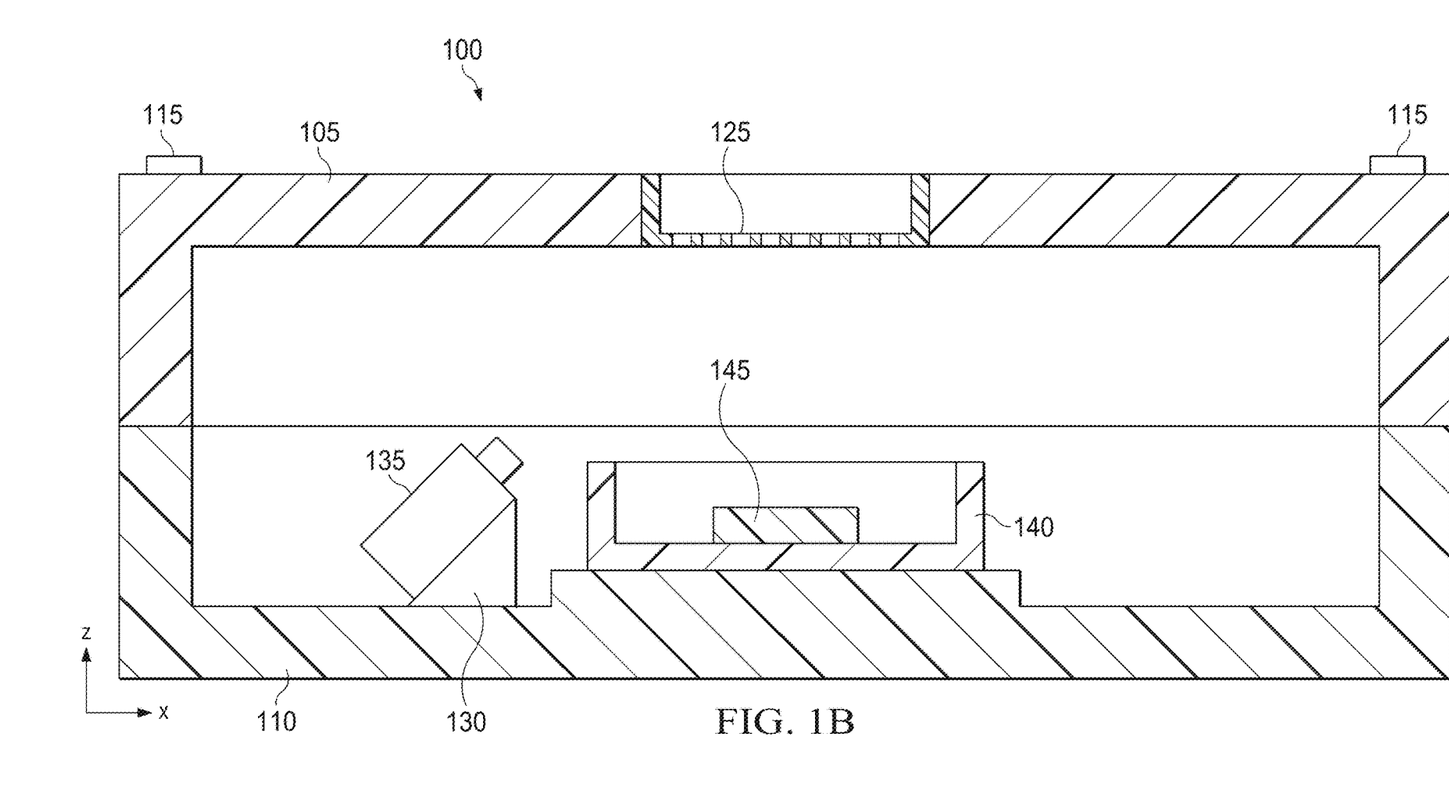
FIG. 1B is a cross-sectional view taken along the 1B-1B cut line of the gas sensor in FIG. 1A.

FIG. 1B is a cross-sectional view taken along the 1B-1B cut line of the gas sensor 100 in FIG. 1A. FIG. 1B shows that the gas sensor 100 comprises the top 105, the bottom 110, and the screws 115. In addition, FIG. 1B shows that the gas sensor 100 further comprises a photonic crystal structure 125, an optical source base 130, an optical source 135, a signal detector base 140, and a signal detector 145. The photonic crystal structure 125 is described below. The optical source base 130 supports the optical source 135 and may comprise Si. The optical source 135 may be a laser diode that serves as an optical pump for light-to-light conversion. For instance, the optical source 135 is a low-wavelength laser that emits light with a wavelength of about 800 nm-1,100 nm. In one example, the wavelength is about 980 nm. Such a light source is less expensive than a mid-IR light source. The signal detector base 140 supports the signal detector 145 and may comprise Si. The signal detector 145 may be a photodetector such as a photodiode.

Figure 1C:
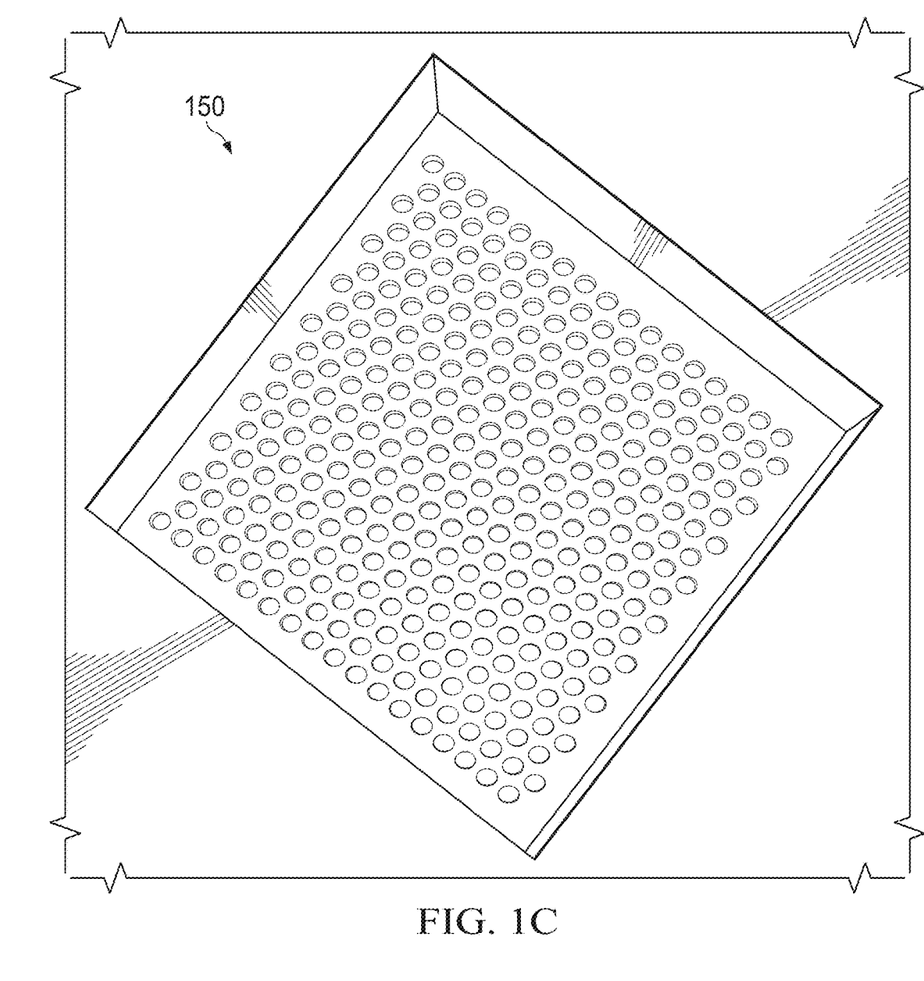
FIG. 1C is a partial top view of the gas sensor in FIG. 1A.

FIG. 1C is a partial top view 150 of the gas sensor 100 in FIG. 1A. The partial top view 150 shows what one would see when looking down into the gas entryway 120. The partial top view 150 shows a grating array, which is part of the photonic crystal structure 125 and is described below.

Figure 1D:
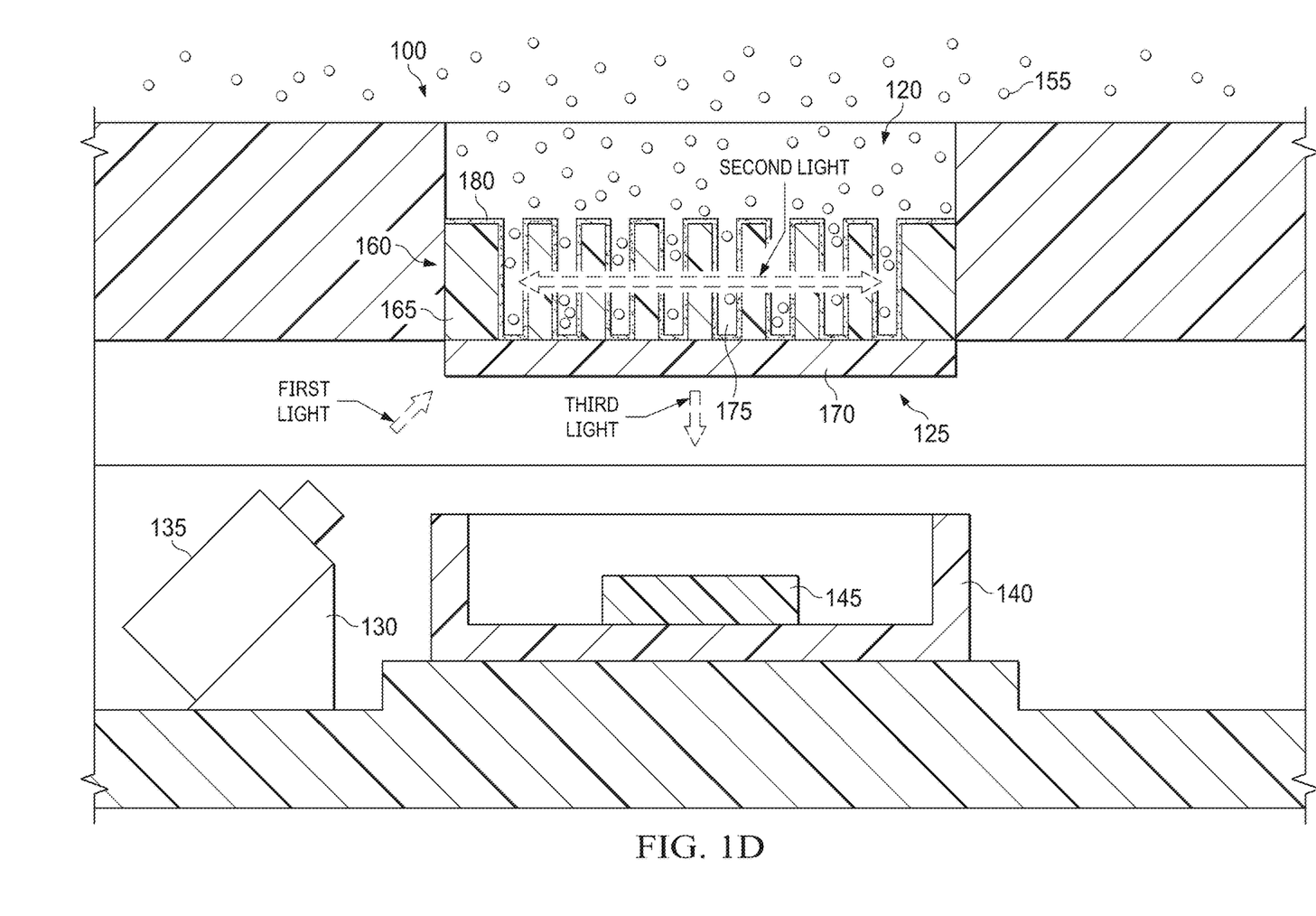
FIG. 1D is another cross-sectional view taken along the 1B-1B cut line of the gas sensor in FIG. 1A.

FIG. 1D is another cross-sectional view taken along the 1B-1B cut line of the gas sensor 100 in FIG. 1A. FIG. 1D shows that the gas sensor 100 comprises the gas entryway 120, the photonic crystal structure 125, the optical source 135, and the signal detector 145. In addition, FIG. 1D shows that the photonic crystal structure 125 comprises a grating array 160, grates 165, a substrate 170, voids 175, and a protective coating 180. The substrate 170 supports the grating array 160 and may comprise a transparent material such as CaF$_2$, BaF$_2$, or ZnSe. The grating array 160 comprises the grates 165, and the grates 165 define the voids 175.

The grates 165 are vertical walls that extend vertically towards the top of the gas sensor 100. Though 7 grates 165 are shown, there may be an array of 8×8-500×500 grates 165. The grates 165 may be substantially equally spaced apart; have substantially equal heights of about 400 nm-2000 nm and widths of about 100 nm-1,000 nm, except for the grates 165 on the left and the right of the page, which may be wider and have widths of about 0.1 mm-5 mm; and comprise a solid-state, group IV-VI Pb-chalcogenide material such as PbSe. "Group IV" refers to the elements of IUPAC group IV (e.g., C, Si, Ge, Sn, and Pb); "group VI" refers to the elements of IUPAC group VI (e.g., S, Se, and Te); and "chalcogenide" refers to a chemical compound, including a sulfide, selenide, telluride, or polonide, that comprises a chalcogen anion and an electropositive element. The grates 165, and thus the larger photonic crystal structure 125, may be called "active" because they radiate light, for instance in the mid-IR range of the electromagnetic spectrum. The mid-IR range comprises wavelengths of about 2.5 μm-12 μm.

The voids 175 accept light and confine gas molecules 155 through a non-linear photonic effect to enhance interaction between light and the gas molecules 155. The gas molecules 155 may enter the gas sensor 100 through the gas entryway 120, move above the grating array 160, and move into the voids 175. The gas molecules 155 vibrate at specific frequencies and thus absorb light at matching frequencies, for instance the mid-IR range.

The protective coating 180 is a thin coating that protects the grates 165 from external elements such as humidity and extreme temperatures, while not affecting the sensing functionality of the gas sensor 100. The protective coating 180 may be about 10 nm-100 nm thick. The protective coating 180 may be a dielectric material such as SiO$_2$.

Manufacturing of the photonic crystal structure 125 is as follows: First, a manufacturer uniformly grows a smooth, uniform layer of the grating array 160 material on the substrate 170 using any combination of PVD, CBD, or other suitable techniques to obtain a smooth surface. Second, the manufacturer performs any combination of maskless laser lithography, e-beam lithography, reactive ion etching, dry etching, or other suitable techniques to etch away portions of the grating array 160 to reveal the voids 175. Third, the manufacturer applies a dielectric film on the structure using an RF magnetron sputtering system.

In operation, the gas molecules 155 enter the gas sensor 100 through the gas entryway 120. The gas molecules 155 then travel towards the grating array 160 and become confined in the voids 175. Meanwhile, the optical source 135 emits first light. The first light may be low-wavelength light. For instance, the first light may have a wavelength in a range of about 800 nm to about 1,100 nm. In one example, the first light has a wavelength of about 980 nm.

The first light travels towards the grates 165, which absorb the first light and radiate second light in response.

The second light may be mid-IR light. For instance, the second light has a wavelength in a range of about 2.5 µm to about 12 µm, or in a range of about 3.0 µm to about 4.8 µm, or more particularly, in a range of about 3.6 µm to about 3.8 µm. Because the optical source 135 provides the first light as a source for the grates 165 to radiate the second light, the optical source 135 may be referred to as an "optical pump."

The second light resonates back and forth between the left grate 165 and the right grate 165 and into the voids 175. Some of the gas molecules 155 in the voids 175 absorb the second light to reduce the total amount of the second light. For instance, the gas molecules 155 are $H_2S$ molecules that absorb light with a wavelength of about 3.6 µm-3.8 µm. The resonation of the second light slows down the second light and lengthens an interaction time with the gas molecules 155 to enhance the absorption of the gas molecules 155.

The second light that remains after absorption by the gas molecules 155, or a portion thereof, travels down as third light towards the signal detector 145. The third light has a wavelength in the same range as the second light. The signal detector 145 converts the third light into an electrical signal. As described below, a computer may analyze the electrical signal and cause an alarm to sound in response to detecting the gas molecules 155. A signal strength of the electrical signal directly correlates to the concentration of the gas molecules 155 and thus the absorption of the second light and the reduction of the third light, so the signal strength decreases when absorbing gas molecules 155 are present in the voids 175.

Though the second light is described as having a wavelength of about 3.6 µm-3.8 µm, the grates 165 may radiate light in a broader range of about 2.5 µm to about 12 µm. Thus, the gas sensor 100 may detect other gases, including both natural gases and acidic gases, that absorb wavelengths in that range. For instance, the gas sensor 100 detects hydrocarbons such as $C_1$, $C_2$, $C_3$, and $C_4$ and acidic gases such as $CO_2$.

Though a first detection is described with respect to the optical source 135, the first light, interaction of the gas molecules 155 with the second light, the third light, and the signal detector 145, the gas sensor 100 may further perform a second detection. For instance, the gas sensor 100 comprises a second optical source that emits a fourth light, which does not interact with the gas molecules 155, but is then detected by a second signal detector. The gas sensor 100 uses the second detection as a baseline detection, or control detection, and the gas sensor 100 determines a differential signal between the first detection and the second detection. The differential signal obviates the need for frequent calibration of the gas sensor 100, thus further improving safety.

Figure 2A:
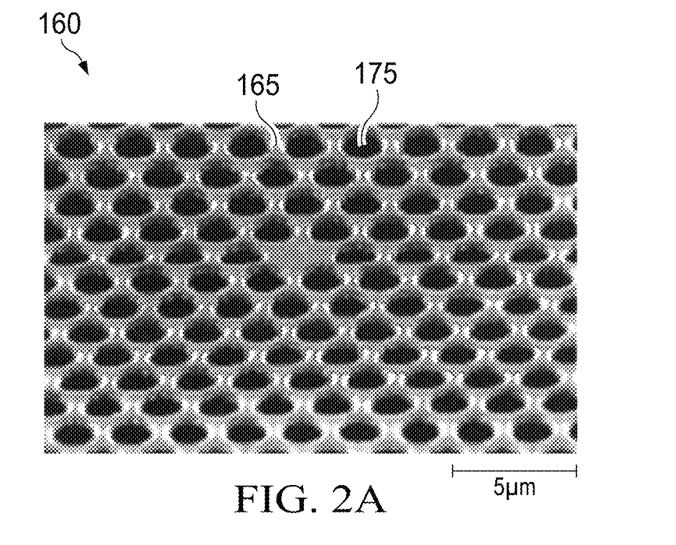
FIG. 2A is a top photographic view of the grating array in FIG. 1D.

FIG. 2A is a top photographic view 200 of the grating array 160 in FIG. 1D. As shown, the grating array 160 comprises grates 165, which defines voids 175. The grating array 160 forms a honeycomb pattern in a 2D grid. Walls of the grates 165 are circular or ovular, so the grates 165 extend cylindrically down towards the substrate 170. Centers of contiguous voids 175 are spaced about 2.5 µm apart. Thus, when a first void 175 and a second void 175 have a third void 175 in between, centers of the first void 175 and the second void 175 are spaced about 5.0 µm apart as shown.

Figure 2B:
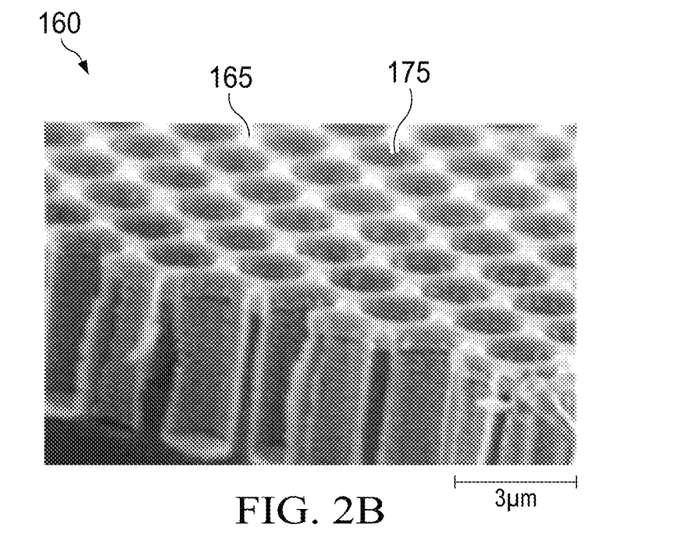
FIG. 2B is a perspective photographic view of the grating array in FIG. 1D.

FIG. 2B is a perspective photographic view of the grating array 160 in FIG. 1D. FIG. 2B shows that the grating array 160 comprises grates 165 arranged in a 2D grid, which may be referred to as a "forest."

Figure 3:
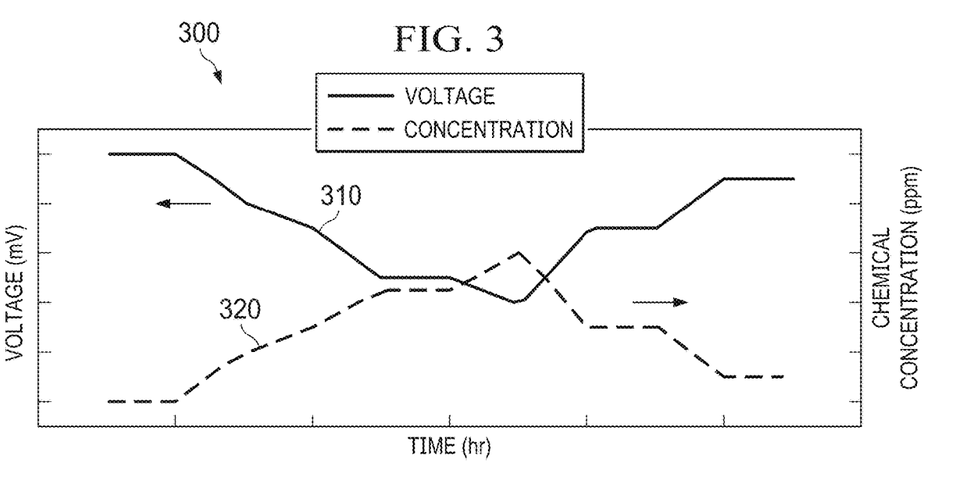
FIG. 3 is a graph showing a relationship between an electrical signal and a gas concentration in the gas sensor in FIGS. 1A-1B and 1D.

FIG. 3 is a graph 300 showing a relationship between an electrical signal and a gas concentration in the gas sensor 100 in FIGS. 1A-1B and 1D. The electrical signal is represented in mV, and the gas concentration is represented in ppm. As shown, when the gas concentration increases, the electrical signal immediately decreases. Thus, the gas sensor 100 displays significant sensitivity.

Figure 4:
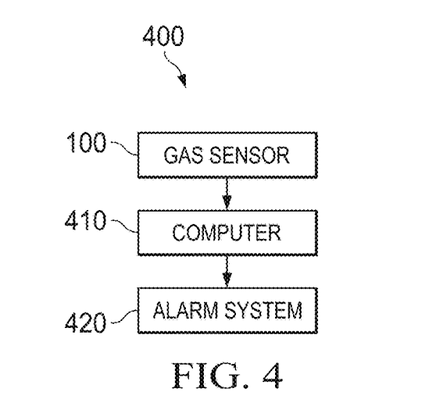
FIG. 4 is a gas sensor system.

FIG. 4 is a gas sensor system 400. The gas sensor system 400 comprises the gas sensor 100, a computer 410, and an alarm system 420. The computer 410 receives from the gas sensor 100 the electrical signal described above, analyzes the electrical signal to determine whether the electrical signal exhibits a "fingerprint" of a gas in the gas sensor 100, and causes the alarm system 420 to provide an alarm when the electrical signal exhibits the fingerprint. The alarm may be an audible alarm such as a siren or a visual alarm such as a flashing light. Alternatively, the computer 410 and the alarm system 420 are part of the gas sensor 100.

Figure 5:
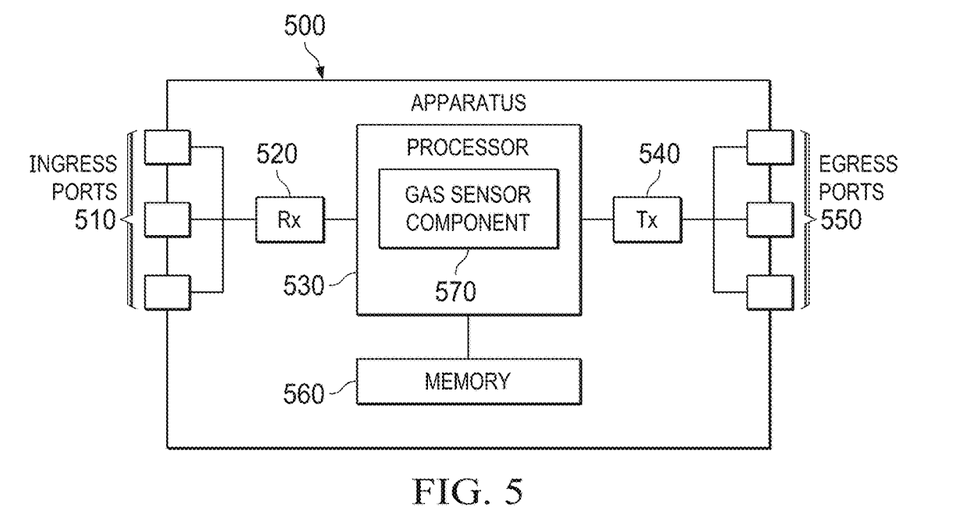
FIG. 5 is a schematic diagram of an apparatus according to an embodiment of the disclosure.

FIG. 5 is a schematic diagram of an apparatus 500 according to an embodiment of the disclosure. The apparatus 500 may implement the disclosed embodiments, for instance the computer 410. The apparatus 500 comprises ingress ports 510 and an RX 520 or receiving means to receive data; a processor 530 or logic unit, baseband unit, CPU, or processing means to process the data; a TX 540 or transmitting means and egress ports 550 to transmit the data; and a memory 560 or data storing means to store the data. The apparatus 500 may also comprise OE components, EO components, or RF components coupled to the ingress ports 510, the RX 520, the TX 540, and the egress ports 550 to provide ingress or egress of optical signals, electrical signals, or RF signals.

The processor 530 is any combination of hardware, middleware, firmware, or software. The processor 530 comprises any combination of one or more CPU chips, cores, FPGAs, ASICs, or DSPs. The processor 530 communicates with the ingress ports 510, the RX 520, the TX 540, the egress ports 550, and the memory 560. The processor 530 comprises a gas sensor component 570, which implements the disclosed embodiments. The inclusion of the gas sensor component 570 therefore provides a substantial improvement to the functionality of the apparatus 500 and effects a transformation of the apparatus 500 to a different state. Alternatively, the memory 560 stores the gas sensor component 570 as instructions, and the processor 530 executes those instructions.

The memory 560 comprises any combination of disks, tape drives, or solid-state drives. The apparatus 500 may use the memory 560 as an over-flow data storage device to store programs when the apparatus 500 selects those programs for execution and to store instructions and data that the apparatus 500 reads during execution of those programs, for instance as a computer program product. The memory 560 may be volatile or non-volatile and may be any combination of ROM, RAM, TCAM, or SRAM.

A computer program product may comprise computer-executable instructions stored on a non-transitory medium, for instance the memory 560, that when executed by a processor, for instance the processor 530, cause an apparatus to perform any of the embodiments.

Figure 6:
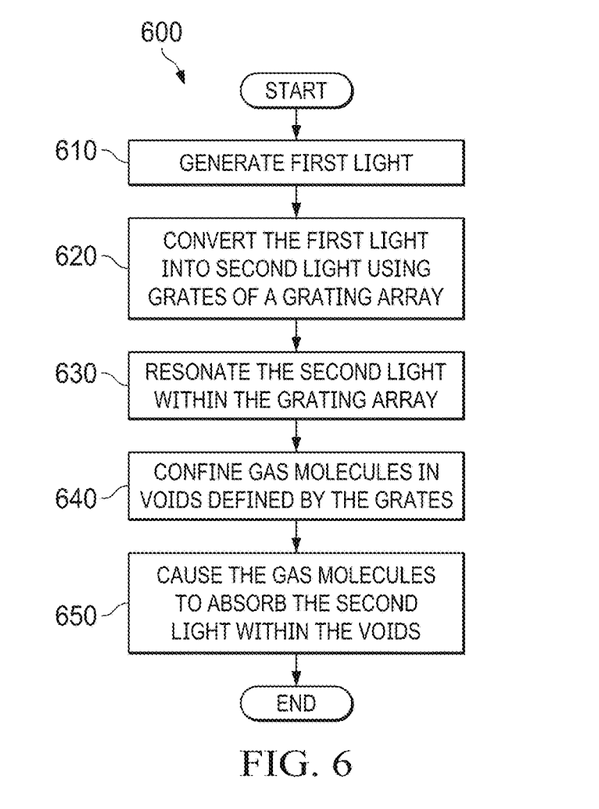
FIG. 6 is a flowchart illustrating a method of gas sensing.

FIG. 6 is a flowchart illustrating a method 600 of gas sensing. The gas sensor 100 implements the method 600, for instance as shown in FIG. 1D. At step 610, first light is generated. For instance, the optical source 135 generates the first light. At step 620, the first light is converted into second light using grates of a grating array. For instance, the grates 165 convert the first light into the second light. At step 630, the second light is resonated within the grating array. For instance, the second light resonates in the grating array 160. At step 640, gas molecules are confined in voids defined by the grates. For instance, the voids 175 confine the gas molecules 155. Finally, at step 650, the gas molecules are caused to absorb the second light within the voids.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A gas sensor system comprising:
   a gas sensor comprising:
      a substrate, a grating array, and a signal detector, wherein:
         (1) the grating array is disposed on a top surface of the substrate and comprises a plurality of grates which define a plurality of voids configured to confine gas molecules for absorption of light and analysis,
         (2) the plurality of grates are configured to absorb a first light having a first wavelength, and convert the first light into a second light having a second wavelength which is greater than the first wavelength, and
         (3) the signal detector is configured to accept a third light remaining after the gas molecules confined in the plurality of voids absorb a portion of the second light, and to convert the third light into an electrical signal.

2. The gas sensor system of claim 1, further comprising a computer operatively coupled to the signal detector and configured to receive the electrical signal therefrom and to analyze the electrical signal to determine if the gas molecules exhibit a predetermined fingerprint.

3. The gas sensor system of claim 2, further comprising an alarm system, wherein the computer is configured to cause the alarm system to issue an alarm when the electrical signal exhibits the predetermined fingerprint.

4. The gas sensor system of claim 3, wherein the alarm is an audible alarm.

5. The gas sensor system of claim 3, wherein the alarm is a visual alarm.

6. The gas sensor system of claim 1, wherein the first wavelength is in a range of about 800 nanometers (nm) to about 1,100 nm.

7. The gas sensor system of claim 1, wherein the first wavelength is about 980 nm.

8. The gas sensor system of claim 1, wherein the second light is mid-infrared (IR) light.

9. The gas sensor system of claim 1, wherein the second wavelength is in a range of about 2.5 micrometers (μm) to about 12 μm.

10. The gas sensor of claim 1, wherein the second wavelength is in a range of about 3.6 μm to about 3.8 μm.

11. The gas sensor system of claim 1, wherein the signal detector is configured to detect hydrogen sulfide ($H_2S$).

12. The gas sensor system of claim 1, further comprising an optical source configured to generate the first light and emit the first light towards the grating array.

13. The gas sensor system of claim 1, further comprising a gas entryway configured to allow the gas molecules to enter the gas sensor.

14. The gas sensor system of claim 1, wherein the substrate and the grating array comprise a photonic crystal structure.

15. The gas sensor system of claim 1, wherein the substrate comprises a transparent material.

16. The gas sensor system of claim 15, wherein the transparent material is calcium fluoride ($CaF_2$), barium fluoride ($BaF_2$), or zinc selenide (ZnSe).

17. The gas sensor system of claim 1, wherein the grating array comprises a group IV-VI Pb-chalcogenide material.

18. The gas sensor system of claim 17, wherein the group IV-VI Pb-chalcogenide material is lead selenide (PbSe).

19. A gas sensing method, comprising:
   providing a gas sensing system comprising a gas sensor, the gas sensor comprising:
      a substrate, a grating array, and a signal detector, wherein:
         (1) the grating array is disposed on a top surface of the substrate and comprises a plurality of grates which define a plurality of voids configured to confine gas molecules for absorption of light and analysis,
         (2) the plurality of grates are configured to absorb a first light having a first wavelength, and convert the first light into a second light having a second wavelength which is greater than the first wavelength, and
         (3) the signal detector is configured to accept a third light remaining after the gas molecules confined in the plurality of voids absorb a portion of the second light, and to convert the third light into an electrical signal; and
   inputting the electrical signal into a computer which is operatively coupled to the signal detector, wherein the electrical signal is analyzed to determine if the gas molecules exhibit a predetermined fingerprint.

\* \* \* \* \*